United States Patent [19]
Bourne et al.

[11] Patent Number: 5,635,134
[45] Date of Patent: Jun. 3, 1997

[54] METHOD OF STERILIZING AN ARTICLE

[75] Inventors: Sonya N. Bourne, Roswell; Nelson McRay, Atlanta; Lavada C. Boggs, Marietta; William R. Neff; Charles J. Morell, both of Roswell; Marsha L. Vaughn, Atlanta, all of Ga.

[73] Assignee: Kimberly-Clark Corporation, Neenah, Wis.

[21] Appl. No.: 468,164

[22] Filed: Jun. 6, 1995

Related U.S. Application Data

[62] Division of Ser. No. 381,060, Jan. 31, 1995, which is a continuation of Ser. No. 84,851, Jun. 30, 1993, abandoned.

[51] Int. Cl.$^6$ .................................................. A61L 2/18
[52] U.S. Cl. ........................................... 422/26; 422/34
[58] Field of Search ................................. 422/26, 34

[56] References Cited

U.S. PATENT DOCUMENTS

| | | | |
|---|---|---|---|
| Re. D 288,048 | 5/1976 | Jezic | 428/212 |
| 3,761,013 | 9/1973 | Schuster | 206/439 |
| 3,780,857 | 12/1973 | Rosano, Jr. et al. | 206/370 |
| 3,809,077 | 5/1974 | Hansen | 128/132 D |
| 4,041,203 | 8/1977 | Brock et al. | 428/157 |
| 4,196,245 | 4/1980 | Kitson et al. | 428/198 |
| 4,287,251 | 9/1981 | King et al. | 428/198 |
| 4,342,392 | 8/1982 | Cox | 206/438 |
| 4,344,999 | 8/1982 | Gohlke | 428/212 |
| 4,355,066 | 10/1982 | Newman | 428/286 |
| 4,380,485 | 4/1983 | Schuster | 156/254 |
| 4,508,113 | 4/1985 | Malaney | 128/849 |
| 4,522,203 | 6/1985 | Mays | 128/849 |
| 4,555,811 | 12/1985 | Shimalla | 2/51 |
| 4,618,524 | 10/1986 | Groitzsch et al. | 428/198 |
| 4,644,586 | 2/1987 | Padgett | 383/102 |
| 4,705,171 | 11/1987 | Eldridge . | |
| 4,793,483 | 12/1988 | Holmes | 206/363 |
| 4,863,785 | 9/1989 | Berman et al. | 428/297 |
| 4,904,520 | 2/1990 | Dumas et al. | 428/212 |
| 5,028,468 | 7/1991 | Taylor | 428/71 |
| 5,072,832 | 12/1991 | Valentine et al. . | |
| 5,222,507 | 6/1993 | Taylor | 128/849 |
| 5,222,600 | 6/1993 | Stoddard et al. | 206/370 |
| 5,229,191 | 7/1993 | Austin | 428/286 |
| 5,244,718 | 9/1993 | Taylor et al. . | |
| 5,283,106 | 2/1994 | Sieler et al. | 428/284 |
| 5,415,925 | 5/1995 | Austin et al. | 428/284 |

FOREIGN PATENT DOCUMENTS

| | | |
|---|---|---|
| 0307173 | 3/1989 | European Pat. Off. . |
| 0155149 | 9/1989 | European Pat. Off. . |
| 0398611 | 11/1990 | European Pat. Off. . |
| 0 398 611 | 11/1990 | European Pat. Off. ......... D06N 3/14 |
| 0405793 | 1/1991 | European Pat. Off. . |
| 0294178 | 5/1992 | European Pat. Off. . |
| 0212540 | 11/1992 | European Pat. Off. . |
| 3835016 | 4/1990 | Germany . |
| 1488326 | 10/1977 | United Kingdom . |
| 1519172 | 7/1978 | United Kingdom . |
| 2132939 | 7/1984 | United Kingdom . |
| 2229110 | 9/1990 | United Kingdom . |
| WO89/11392 | 11/1989 | WIPO . |
| WO90/00643 | 1/1990 | WIPO . |
| WO91/02643 | 3/1991 | WIPO . |
| Wo92/05074 | 4/1992 | WIPO . |

*Primary Examiner*—Robert J. Warden
*Assistant Examiner*—Theresa T. Snider
*Attorney, Agent, or Firm*—David J. Alexander; Doug H. Tulley

[57] ABSTRACT

Disclosed herein is a single step sterilization wrapping material suitable for use, as an example, in wrapping surgical instruments and supplies for sterilization, transportation and storage. The material includes separate inner and outer wraps which, unlike previous wraps, are joined to one another. Common wrapping techniques involve wrapping items to be sterilized with two separate sheets of wrap. The present invention provides separate wraps which can be specially engineered to deliver specific properties for each sheet and then joined to one another so as to permit wrapping and opening in a neat single step process which increases efficiency and saves time and money. In special situations the outer wrap can be engineered with increased strength, the inner wrap with increased barrier properties and the inner and outer wraps can be made visually distinct from one another so that improper wrapping or opening is not a problem.

19 Claims, 2 Drawing Sheets

METHOD OF STERILIZING AN ARTICLE

This application is a divisional application Ser. No. 08/381,060, now abandoned, entitled "SINGLE STEP STERILIZATION WRAP SYSTEM" and filed in the U.S. Patent and Trademark Office on Jan. 31, 1995 which was a continuation application of application Ser. No. 08/084,851, now abandoned, entitled "SINGLE STEP STERILIZATION WRAP SYSTEM" and filed in the U.S. Patent and Trademark Office on Jun. 30, 1993.

BACKGROUND OF THE INVENTION

The present invention is directed to sterilization wrap materials. More particularly, the present invention is directed to multi-plied materials made from individual sheets which are fused together so as to be suitable for use as a sterilization wrap for wrapping surgical instruments and supplies for sterilization and storage in conjunction with surgical procedures and for other applications such as packaging items for bone marrow units.

Personnel in the Central Service Room (CSR) or the Sterile Processing Department (SPD) of hospitals are commonly charged with the responsibility of packaging surgical supplies to ensure that the sterility of the packaged contents are maintained all the way from sterilization to the point of reuse. Several activities are involved in the task of sterile supply delivery to the operating room and other units.

Much of the surgical instruments and supplies used in the operating room are reusable. These supplies typically include such things as clamps, scalpel blade handles, retractors, forceps, scissors, surgeons towels, basins and the like. All of these supplies must be collected after each procedure and sterilized before they can be used again in another procedure. To this end, the supplies are placed in stainless steel instrument trays, and soft goods such as surgeons towels, drapes, and gowns are prepared for packaging. Then, the trays and package contents are each generally wrapped with two sheets of material commonly referred to as sterilization wrap.

The sterilization wrap is usually a woven or nonwoven material which when wrapped around the tray or package contents in a certain prescribed manner will permit the entry of sterilizing vapor/gas or other medium to sterilize the contents of the tray while denying the ingress of contaminants such as bacteria and other infectious causing materials or their vehicles after sterilization. Generally, the two primary means for sterilizing instruments are autoclaving with steam and ethylene oxide sterilization.

Using a wrapped tray as an example, once the wrapped tray and its contents have been sterilized, the wrapped tray is transported to the point of use, typically an operating room, or is stored until it is ready to be used. During storage and transfer to the operating room, the wrapped tray may be handled several different times. Each time the wrapped package is handled, there is a potential that the sterile nature of the package contents can be compromised. The two most common ways the wrapped package can be compromised are a tear or other breach of the wrapping material, and wetness or foreign materials identified on the outer wrapper, which would warrant a premature unwrapping.

In order to promote and maintain the sterility of the packaged contents, the Association of Operating Room Nurses (AORN) has developed certain recommended practices for the wrapping and handling of in-hospital processed packages. It is common practice among many hospitals as recommended by the AORN to "double wrap" in-hospital processed packages. A primary method of double wrapping is "sequential" in nature in that the package contents are first wrapped by one sheet of sterilization wrap and then wrapped again by another sheet of sterilization wrap. Another method of double wrapping is "simultaneous" in nature in that the package contents are wrapped by two sheets of sterilization wrap at the same time. That is, two sheets of sterilization wrap are aligned one on top of the other, and the item to be wrapped is placed on top of the two sheets, then the item is wrapped by both sheets of material at the same time.

Studies have been used to track packages from initial wrapping, all the way through sterilization, storage, handling, transfer, unwrapping and ultimate reuse. These studies indicate that the frequency of compromising wrapped items due to tears or holes has been reduced because of improved handling and storage techniques and because of improved sterilization packaging products. One of the main thrusts behind such efforts has been economics. Every time a sterile package is compromised, it must be taken out of circulation, unwrapped, rewrapped, and resterilized before it can properly be reused. This wastes time and money.

While the frequency of compromising wrappers has been reduced thus resulting in the saving of time and money, the use of simultaneous wrapping techniques would further increase the time savings in wrapping and opening packages and thus result in a still greater cost savings. Simultaneous wrapping takes less time than sequential wrapping and recent research in hospitals has shown simultaneous wrapping to be just as effective as sequential wrapping in maintaining sterility absent a breach in the wrap which is generally independent of the manner of wrapping.

Even though the hospital staff may desire to simultaneously wrap instead of sequentially wrap, the time it takes to set up the outer and inner sheet wrappers and the awkwardness of manipulating loose wrappers during simultaneous wrapping can offset the time savings hoped to be achieved when attempting to move away from sequential wrapping. Consequently, if a product existed which provided the appropriate inner and outer sheet combinations and eliminated the awkwardness of keeping the two sheets together during the package wrapping and opening processes, then a simultaneous packaging system would deliver the benefits desired including time savings and targeted engineered inner and outer sheet performance.

In conjunction with the manner in which the packages are wrapped, the material used for wrapping is also important. As mentioned above, the two most common wrapping materials are woven materials such as cloth (cotton/polyester), nonwoven materials such as KIMGUARD® Sterile-Wrap (polypropylene) from Kimberly-Clark Corporation of Neenah Wisconsin and Bio-shield CSR Wrap (wood pulp/polyester) from Baxter Healthcare Corporation of Deerfield, Ill. One version of the Baxter sterilization wrap is a product called DualWrap® Sterilization Wrap, which includes an inner sheet of wet laid paper (cellulose) and a separate outer sheet of spunlaced or hydroentangled pulp/polyester. The inner and outer layers are provided in a stack of loose, unattached sheets in which the inner and outer sheets are alternated.

Whatever the material is that is being used as sterile wrap, it should be noted that when wrapping two sheets at the same time, it is important that the wrapping materials provide good barrier properties to maintain package sterility and good strength properties so that tearing or other forms of breaching are held to a minimum. If the outer and inner sheets of the double wrap are to have different properties, then it is important that the system be visually identifiable so that the user can determine which wrapper is the outer sheet and which wrapper is the inner sheet. Consequently, there is a need for a new sterilization wrap system that actually reduces the time for packaging and opening and delivers outer and inner sheet engineered performance in a simple identifiable and easy to use fashion. Such attributes are provided by the present invention as will become more apparent upon a further review of the following specification, claims and drawings.

SUMMARY OF THE INVENTION

Disclosed herein is a single step sterilization wrap system for wrapping items in packages which are to be sterilized and maintained in a sterilized condition until use such as surgical instruments for hospital operating room use. A large number of such items are currently wrapped by two separate sheets of sterilization wrap. The most common method of wrapping such items is called double, sequential wrapping wherein an item is wrapped in a first piece of sterilization wrap with the loose ends being taped shut. Next, a second and separate sheet of sterilization wrap is used to wrap the item a second time. Once the second sheet of wrap has been wrapped around the item, the loose ends of the second sheet are taped closed and the wrapped item is sent through a sterilization process. After the wrapped item has been sterilized, it is normally placed in storage until actual use at which time the wrapped and sterilized package is removed from storage and transported to the operating room where the sterile wrap is removed and the items are subsequently used. A second and less commonly used method of wrapping is called the simultaneous wrapping wherein two sheets of sterilization wrap are placed one on top of the other, aligned and then the two sheets are wrapped about the item to be sterilized at the same time. After wrapping is complete, the loose ends are taped shut and the item is sent through the same sterilization process as described above.

The present invention provides an improved means for simultaneously wrapping and unwrapping items which must be sterilized prior to use. This is accomplished by bonding or joining two separate sheets of sterilization wrap together at one or more locations to create a single step system wherein the separate sheets are prealigned and joined to one another to facilitate the wrapping process as well as the unwrapping process. As a result, the amount of time needed to wrap and unwrap an item is decreased and the ease of wrapping is improved. In addition, each of the individual sheets of the single step sterilization wrap system can be specifically engineered or designed to impart special or different features to the overall system.

The single step sterilization wrap system includes an outer wrap made from a first sterilization sheet which is superposed on an inner wrap made from a second sterilization sheet with each of the sheets being independent of one another and joined to one another at one or more bond sites. The individual inner and outer wraps can be made from a variety of sterilization materials including fibrous materials such as nonwovens and wovens. The sterilization wrap system has a first exterior surface and a second exterior surface formed by the opposed sides of the system with each of the surfaces having respective surface area and wherein the bond sites joining the inner and outer wraps together occupy no more than 50% of the surface area of either the first or second exterior surfaces of the sterilization wrap system. The inner and outer wraps can be joined to one another in a variety of bonding patterns including both long continuous seams and point bonding. If desired, the sterilization wrap system can define a first zone and a second zone with the first zone having a greater number of the bond sites than the second zone and wherein the second zone is surrounded by the first zone so that the sterilization wrap system has an area of low density bonding surrounded by an area of higher density bonding.

Each of the individual sheets can be designed to have particular properties which may be the same or different from the other sheet of the single step sterilization wrap system of the present invention. For example, the outer wrap can be made stronger than the inner wrap as indicated by the outer wrap having a greater grab tensile strength as compared to the inner wrap. In addition, the barrier properties of the inner wrap can be fortified to create a better means of filtering bacteria than the outer wrap.

The inner wrap and outer wrap can both be made from nonwoven laminates such as spunbond/meltblown/ spunbond laminates wherein the inner meltblown layer provides barrier properties and the outer spunbond layers provides strength. By using a heavier basis weight meltblown layer in the inner wrap as compared to the outer wrap, the inner wrap will have a better barrier property than the outer wrap in which case the inner wrap will have a lower dry spore penetration rate than the outer wrap and a greater bacterial filtration efficiency than the outer wrap. Conversely, the meltblown layer of the inner wrap can be decreased to such an extent that the bacterial filtration efficiency of the inner wrap is less than the outer wrap. Furthermore, the strength of the inner and outer wraps can be varied by varying the basis weight and the types of polymers being used to form the fibers which make up the individual layers of the respective laminates. As a result, a sterilization wrap system can be designed wherein the peak energy of the outer wrap is greater than the inner wrap.

In situations where the inner wrap has different design properties than the outer wrap, is important that the end user be able to determine which of the two wraps (inner or outer) should be placed adjacent the item being wrapped and subsequently sterilized. To this end, the inner and outer wraps can be designed so as to be visually distinct from another as by printing or other indicia as well as the use of different colors or shades with respect to the individual sheets of sterilization wrap.

DETAILED DESCRIPTION OF THE INVENTION

Disclosed herein is a sterilization system suitable for use with simultaneous wrapping procedures for wrapping, sterilizing, storing and using sterilized items such as surgical supplies. While the present invention will be described in conjunction with its use in hospital and surgical room procedures, the sterilization system of the present system is intended for use wherever there is a need for sterilized materials. Consequently, the following description of the present invention should not be considered a limitation as to the scope of use of the present invention.

Figure 1:
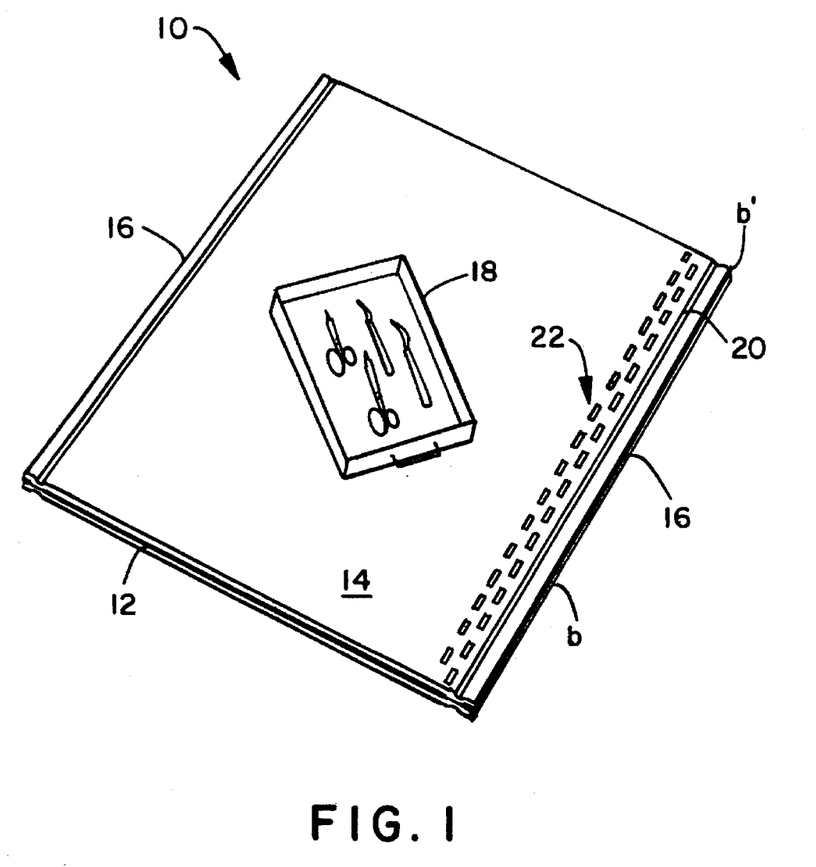
FIG. 1 is a perspective view of a single step sterilization wrap according to the present invention with a sterilization tray ready for wrapping placed on top of the sterilization wrap.
Figure 2:
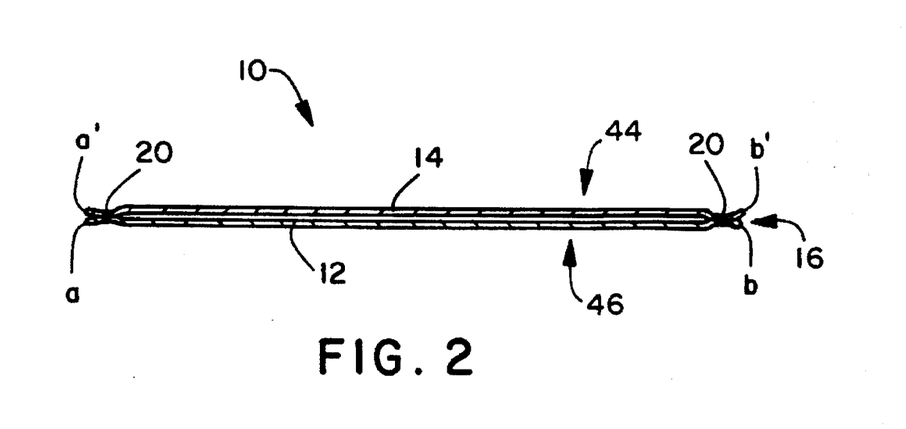
FIG. 2 is a cross-sectional side view of a single step sterilization wrap according to the present invention.

Referring to FIGS. 1 and 2 of the drawings, there is shown a sterilization system or wrap for containing and maintaining sterility of surgical supplies and the like. The sterilization system 10 includes an outer wrap 12 also referred to as a strength reinforced barrier web laminate and an inner wrap 14 also referred to as a barrier web laminate. As can be seen from FIG. 1, the outer wrap 12 and inner wrap 14 are placed in face to face relationship with one another, one on top of the other in vertical juxtaposition. Each of the wraps are of the same general size and shape. Most typically the wraps will be square or rectangular in shape. As a result, each wrap will have at least two generally parallel edges a,a' and b,b' located about their peripheries 16.

To facilitate wrapping of an item 18 such as is shown in FIG. 1, the outer wrap 12 and the inner wrap 14 are attached to one another in a manner so as to hold the two wraps together while still maintaining their visual distinctiveness so that the end user can visually see that the item is being wrapped by two separate sheets of sterile wrap. Generally the two wraps will be joined about all or a portion of their peripheries 16. As specifically shown in FIGS. 1 and 2, the two wraps are joined to one another along the entire length of two generally parallel edges of the wrap, a–a' and b–b'. The edges can be joined to one another by any number of suitable means including, but not limited to, adhesives, stitching, heat bonding and ultrasonic bonding collectively referred to as joining. As shown in FIGS. 1 and 2, the bond sites 20 are perfected by ultrasonic bonding, are continuous, and run the entire length of the edges just interior to or along the periphery 16 on opposed sides of the sheets 12 and 14.

In addition to or as an alternate to the continuous bonds or seams 20, a second set of bonds 22 may be used to secure the two wraps together. The bonds 22 in FIG. 1 are a series of spaced-apart and separate bond points in the form of two rows of parallel but spaced apart rectangles or other shapes with the rectangles in one row being offset from the other row so that they are in overlapping relationship if the system 10 were viewed edge on. This bond pattern has been used to seam sleeves on disposable surgical gowns manufactured by the assignee of record, Kimberly-Clark Corporation of Neenah, Wisconsin. The bonds 22 can be just interior of the continuous bonds 20 and serve to further join the two wraps 12 and 14 together when used alone or in conjunction with the continuous bonds 20.

Figure 3:
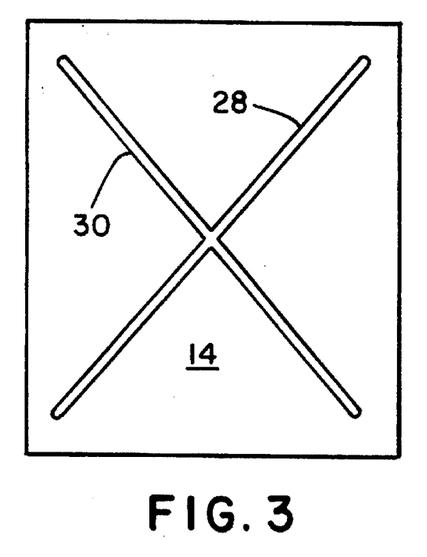
FIGS. 3 through 6 are top plan views of additional single step sterilization wraps according to the present invention with different bonding patterns for joining the separate sterilization wrap sheets together.
Figure 4:
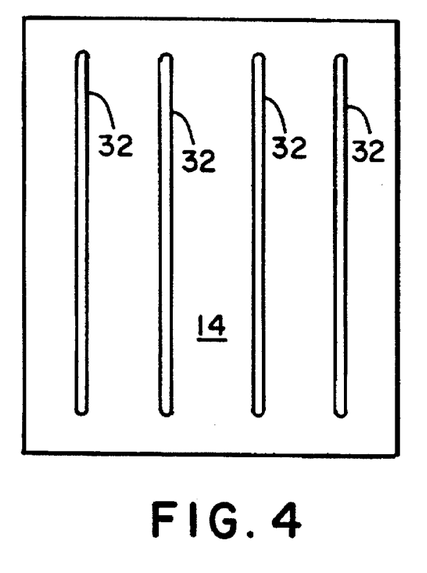
Figure 5:
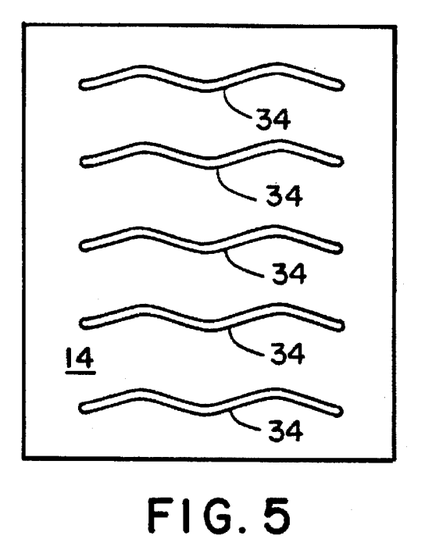
Figure 6:
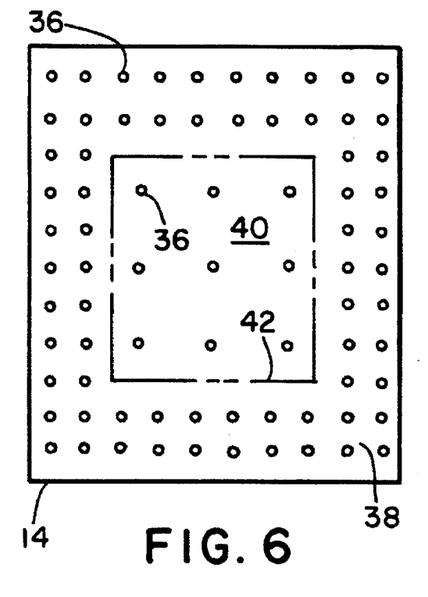

It also is possible to effect bonding between the two wraps 12 and 14 in a variety of other manners which are exemplified, at least in part, in FIGS. 3 through 6. In FIGS. 3 through 6, the inner and outer wraps are superposed and joined to one another by one or more bond sites which may be long continuous bond lines such as are shown in FIGS. 3 through 5 or a plurality of localized bond points such as are shown in FIG. 6. In FIG. 3, which is a top plan view, the outer wrap 12 and inner wrap 14 of the system 10 are bonded together by two crisscrossing bond lines 28 and 30 which form a "X"-pattern across the surface of the system 10. In FIG. 4, the outer wrap 12 and the inner wrap 14 of the system 10 are bonded to one another by a series of parallel bonds 32 which span all or a portion of the length or width of the system 10. In FIG. 5, a series of sinusoidal bonds 34 are provided.

In addition to or in conjunction with the relatively long bonds or seams shown in FIGS. 3 through 5, the outer wrap 12 and the inner wrap 14 of the system 10 may be joined by a plurality of localized, discontinuous bond points 36 such as are shown in FIG. 6. These bond points may be uniformly spaced across the surface of the system 10 or they may be broken into two or more zones with each of these zones having varying degrees or densities of bond sites. Referring specifically to FIG. 6, the system 10 is divided into a first zone 38 and a second zone 40 which, for purposes of illustration, are shown in FIG. 6 as being separated by an imaginary dashed line 42. The first zone 38 has a greater number of the overall plurality of bond sites per unit area than the second area 40. In addition, the first zone 38 completely surrounds the second zone 40 thereby creating a system 10 wherein the periphery of the system 10 has a generally greater degree of bonding than the central portion of the system 10.

Other combinations of bonding patterns can also be used. For example, indicia, logos and other printed matter can be used as the bond pattern to bond the outer wrap 12 to the inner wrap 14. Thus the bond pattern could be wording such as "KIMBERLY-CLARK" or "KIMGUARD®".

An important feature of the present invention is that the user of the single step sterilization wrap system of the present invention can visually perceive that the system does in fact include two separate sheets of sterilization wrap. Being able to see this reinforces the comfort level of the user that the wrapped item is protected by not one but two sheets of sterilization wrap. Thus the two sheets of sterilization wrap should be joined to one another with a sufficient amount of bonding so that the two sheets do not separate, but not with so much bonding that the two sheets appear to be one. To this end, the sterilization wrap system 10 can be viewed as having a first exterior surface 44 and a second exterior surface 46 on opposed sides of the system 10. See FIG. 2. To maintain the visual distinctiveness of the two respective surface areas it is advantageous if the surface area of the bond sites do not occupy more than about 50 percent of the surface area of either the first or second exterior surfaces 44 and 46 of the sterilization wrap system 10.

While wishing to maintain the visual distinctiveness of the outer wrap 12 and inner wrap 14, the two sheets of wrap should be sufficiently joined to one another so that they do not readily separate from one another throughout the process of removing the sterilization wrap from its original packaging, wrapping the items to be sterilized with the wrap and unwrapping the sterilized items for use. Consequently, it is desirable that there be at least a one pound tensile force needed to separate the joined sheets from one another.

Generally, the bonded wraps come in several sizes to wrap various size items and trays. Typical sizes include 18, 24, 30, 36, 40, 45, 48 and 54 inch square wrappers as well as 54×72 inch rectangular wrappers. To wrap an item, in this case a sterilization wrap tray 18 such as shown in FIG. 1, the item is placed on top of the system 10 in contact with the inner wrap 14 such that the four corners of the wrap can be folded over onto the package one at a time. Once the folding is completed, the wrap is sealed with tape and the wrapped package is ready to be sterilized.

Each of the wraps can have its own special characteristics. The main function of the inner wrap 14 is to act as the primary filtration barrier while the primary function of the outer wrap 12 is to provide strength with a secondary function of also providing a barrier to bacteria and other contaminants.

Both the outer wrap 12 and the inner wrap 14 can be made from a number of materials. Sterilization wraps are generally characterized as falling into two main classes, reusables and disposables. Reusables are materials which, as the name suggests, can be reused, typically by washing or some other form of cleaning. Disposables, on the other hand, are usually one-use items which are discarded or recycled after their initial use. Generally, cloth, linen or other woven materials fall into the reusable category while disposables normally include nonwoven materials made from either or both natural and synthetic fibers such as paper, fibrous polymeric nonwovens as well as films which are capable of passing sterilants and retarding transmission of bacteria and other contaminants.

Nonwoven sterilization wraps have become particularly well-liked due to their barrier properties, economics and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, polyesters, polyolefins and many other thermoplastic materials. The fibers may be relatively short, staple length fibers, typically less than 3 inches, or longer more continuous fibers such as are produced by spunbonding and meltblowing processes. Whatever materials are chosen, the resultant wrap must be compatible with the particular sterilization technique being used and must also provide both strength and barrier properties to maintain the sterile nature of the wrapped contents until use.

It has been found that polyolefin-based fibers and their resultant nonwovens are particularly well-suited for the production of sterilization wrap. Polypropylene spunbonded nonwovens such as are produced by the Assignee of record, Kimberly-Clark Corporation, can be used to impart strength characteristics to the sterilization wrap and in particular, the outer wrap 12. In more refined embodiments, the outer wrap 12 can be made from laminates such as a laminate of spunbond and meltblown or spunbond, meltblown, spunbond to impart both strength and barrier properties to the outer wrap 12.

A spunbond, meltblown, spunbond material is made from three separate layers which are laminated to one another. The method of making these layers is known and described in commonly assigned U.S. Pat. No. 4,041,203 to Brock et al which is incorporated herein in its entirety by reference. The material of Brock et al is a three layer laminate of spunbond/meltblown/spunbond which is also commonly referred to by the acronym "SMS". The two outer layers of SMS are a spunbond material made from extruded polyolefin fibers laid down in a random pattern and then bonded to one another. The inner layer is a meltblown layer also made from extruded polyolefin fibers generally of a smaller diameter and sometimes having a more discontinuous length than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbond layers provide a greater portion of the strength factor in the overall laminate.

A particular feature of the present invention is the specific tailoring available for each of the layers in the respective outer wrap 12 and inner wrap 14. While the two wraps can be identical to one another, in more refined embodiments of the present invention the outer wrap 12 is designed to have higher strength properties than the inner wrap 14. This is to provide a stronger barrier to tears and other possible breaches of the wrapped item from exterior objects. Conversely, in more refined embodiments of the present invention, the inner wrap 14 is designed to have higher barrier properties than the outer wrap 12. Adjusting the barrier and strength properties can generally be accomplished by adjusting the basis weights of the outer and inner wraps as well as the basis weights of each of the individual layers within each of the wraps. Suitable basis weight ranges for either of the wraps range between about 0.5 and about 3.5 ounces per square yard (osy).

One particular example of a single step sterilization wrap system comprises an outer wrap made from a strength barrier web laminate and an inner wrap made from a barrier web laminate with the strength barrier web laminate and the barrier web laminate being placed adjacent to one another in generally face-to-face or superimposed relationship with the laminates being joined to one another at one or more bond sites. Each of the layers are made from a spunbond/meltblown/spunbond laminate as taught, for example, by U.S. Pat. No. 4,041,203. Thus the strength barrier web laminate can comprise a first strength layer made from randomly deposited fibers, a second strength layer made from randomly deposited fibers and an intermediate barrier layer made from randomly deposited fibers with the fibers in the intermediate barrier layer having an average fiber diameter which is less than the average fiber diameter of the fibers in either of the first or second strength layers. In addition, the intermediate barrier layer is disposed between and bonded to the first and second reinforcing layers. This strength barrier web laminate will generally form the outer wrap 12. The inner wrap 14 can be made from a barrier web laminate comprising a third strength layer made from randomly deposited fibers and a fourth strength layer made from randomly deposited fibers with a second intermediate barrier layer made from randomly deposited fibers. Here again the fibers of the second intermediate barrier layer have an average fiber diameter which is less than the average fiber diameter of either the third or fourth strength layers and the second intermediate barrier layer is disposed between and bonded to the third and fourth strength layers. To provide added strength, the outer wrap comprised of the strength barrier web laminate can have a greater grab tensile strength than the inner wrap and the inner wrap made from the barrier web laminate can have a dry spore penetration rate which is lower than the outer wrap and a bacterial filtration efficiency which is greater than the outer wrap.

When designing inner and outer wraps with different properties it is usually important that system 10 be positioned such that proper wrap surface faces the item to be wrapped and the other wrap surface faces away from the wrapped item. Typically this will mean that the inner wrap 14 is in contact with the item 18 to be wrapped and the outer wrap 12 will be positioned away from the wrapped item 18. To this end it may be desirable to produce inner and outer wraps which are visually distinguishable from one another. By "visually distinguishable" it is meant that a majority of people who routinely use such materials would be able to tell the difference between the first exterior surface 44 and the second exterior surface 46 of the system 10 based upon a visual observation of the two surfaces. One means of achieving this would be shading or coloring the inner wrap 14 differently than the outer wrap 12. In addition, printing or other indicia could be used to differentiate the two wraps from one another.

To demonstrate the attributes of the present invention, several sterilization wrap systems 10 were prepared and then tested against other currently available sterilization wraps. Several of these wraps including samples of the present invention were wrapped around sterilization packages and then sent through a representative in-hospital handling process after which, the contamination rate of the trays was measured. In addition, the attributes of certain components of the present invention were compared to the components of other available products.

Kimberly-Clark Corporation, the assignee of record, manufactures a series of single sheet sterilization wrap materials made from spunbond/meltblown/spunbond laminates. These materials are available in a variety of basis weights as indicated below in Table I.

TABLE I

| Wrap Type | Grade | Basis Weight - total (per layer) (s/m/s) |
| --- | --- | --- |
| SPUNGUARD ® 1 Sterilization Wrap | Light | 1.05 osy (.35/.35/.35) |
| SPUNGUARD ® Sterilization Wrap | Regular | 1.2 osy (.375/.45/.375) |
| SPUNGUARD ® Sterilization Wrap | Heavy Duty | 1.5 osy (.525/.45/.525) |
| SPUNGUARD ® Sterilization Wrap | Super Duty | 1.85 osy (.7/.45/.7) |
| KIMGUARD ® Sterile Wrap | Regular | 1.4 osy (.45/.5/.45) |
| KIMGUARD ® Sterile Wrap | Midweight | 1.8 osy (.65/.5/.65) |
| KIMGUARD ® Sterile Wrap | Heavy Duty | 2.2 osy (.85/.5/.85) |
| KIMGUARD ® Sterile Wrap | Ultra | 2.6 osy (1.05/.5/1.05) |

Two sterilization wrap systems 10 were prepared according to the present invention. One of the two systems had a lower overall basis weight and therefore is referred to as a regular grade. The second sterilization wrap system had a higher overall basis weight, and therefore, was referred to as a heavy grade. The outer wrap 12 of the regular grade system 10 was a spunbond/meltblown/spunbond laminate with an average overall basis weight of 1.4 ounces per square yard. The two outer layers of the outer wrap 12 each had a basis weight of 0.55 ounces per square yard and the inner layer of meltblown had a basis weight of 0.3 ounces per square yard. The inner wrap 14 of the regular grade system 10 had an average overall basis weight of 1.4 ounces per square yard including individual outer spunbond layer basis weights of 0.45 ounces per square yard and an inner meltblown basis weight of 0.5 ounces per square yard. The outer wrap 12 and the inner wrap 14 were ultrasonically bonded together in the same fashion as the bonding shown in FIG. 1 including two continuous bonds along two opposed parallel edges of the system and a series of spaced-apart bonds just interior to each of the continuous seam bonds. The opposite opposed edges were not bonded. The heavy grade sterilization wrap system 10 had an outer wrap 12 made from a spunbond/meltblown/spunbond laminate with an average overall basis weight of 2.6 ounces per square yard. The outer wrap 12 was made from two layers of spunbond each of which had a basis weight of 1.05 ounces per square yard and a middle meltblown layer having a basis weight of 0.5 ounces per square yard. The inner wrap 14 of the heavy duty grade sterilization wrap system 10 was also made from a spunbond/meltblown/ spunbond laminate and had an average overall basis weight of 1.8 ounces per square yard. This wrap 14 included two outer spunbond layers each of which had a basis weight of 0.65 ounces per square yard and an inner layer of meltblown having a basis weight of 0.5 ounces per square yard. The outer wrap 12 and inner wrap 14 were bonded to each other in the same fashion as the regular grade sterilization wrap system described above. These two systems according to the present invention were tested against two sheets of unattached sterilization wrap produced by Baxter Healthcare of Deerfield, Ill. and sold as DualWrap® sterilization wrap. The DualWrap® sterilization wrap is sold to customers in a box in loose sheet form with a hydroentangled outer sheet and a paper-based inner sheet alternated in the box and with the individual sheets being unattached to one another. The DualWrap® sterilization wrap had an overall basis weight including both sheets of 3.57 ounces per square yard. This wrap included a heavier outer sheet with a basis weight of 2.02 ounces per square yard and a lighter inner sheet with a basis weight of 1.55 ounces per square yard. Each of the individual sheets of the samples were tested in the machine and cross-directions for grab tensile strength in pounds and peak energy in inch-pounds. The samples were also tested for dry spore penetration in parts per thousand and bacterial filtration efficiency as a percentage. Each of the samples were also tested for Frazier porosity in cubic feet per square foot per minute. The grab tensile strength and peak energy measurements were performed in accordance with Federal Test Method Standard 191A, method 5100 as modified by 1992 protocol. The dry spore talc filtration efficiency test measures the ability of a fabric to resist the penetration of bacteria on dry talc particles. A stream of air, moving at one cubic foot per minute and carrying talc particles with a range of average diameters of 1 to 9 microns, was pumped through the sterilization wrap to agar-filled petri dishes below. Attached to the particles was Bacillus Subtilis, var. Globgii. The dishes were cultured at 37° C. (plus or minus 2° C.) for 24 hours. Bacterial colonies were then counted to determine the filtration efficiency and the efficiencies were then reported as the number of particles per one thousand penetrating particles. This testing was performed on the individual sheets pursuant to standard operating procedure ARO-003.

The bacterial filtration efficiency test is a measurement of the ability of a material to prevent the passage of bacteria completely through itself. To determine this, a culture of *Staphylococcus aureus* was diluted in 1.5% peptone water to a precise concentration. The culture suspension was pumped through a 'Chicago' nebulizer at a controlled flowrate and fixed air pressure. The constant challenge delivery at a fixed air pressure formed aerosol droplets with a mean particle size (MPS) of approximately 3.0 um. The aerosol droplets were generated in a glass aerosol chamber and drawn through a six-stage, viable particle, Andersen sampler which contained single sheets of the various wraps being tested. The collection flowrate through the test sample and Anderson sampler was maintained at 28.3 LPM (1 CFM). Test controls and test samples were challenged for a 2 minute interval. A total of five samples were run for each of the materials tested.

The delivery rate of the challenge also produced a consistent level of 2200±500 colony forming units (CFU) on the test control plates. A test control was run using no filter medium in the airstream. The requirement for the test control was that the control average fell within the range of 1700–2700 colony formed units (cfu). Test controls were run 4 to 5 times a day. A reference material was also included after every set of test samples. The standard reference material used had filtration efficiencies of 97.5%±1.0.

The Anderson sampler, a sieve sampler, impinged the aerosol droplets onto the six agar plates based on the size of each droplet. The agar medium used was soybean casein digest agar (SCDA). The agar plates were incubated at 37° C.±2° C. for 48 hours and the colonies formed by each bacteria laden aerosol droplet counted and converted to 'probable hit' values using the hole conversion chart provided by Andersen. These converted counts were used to determine the challenge level delivered to the test samples. The distribution ratio of colonies for each of the six agar plates were used to calculate the mean particle size (MPS) of the challenge aerosol. The filtration efficiencies were calculated as a percent difference between test sample runs and the control average using the following equation:

$$BFE\% = \frac{C-T}{C} \times 100$$

Where: $C$ = Average of control values.

$T$ = Count total for test material.

The Frazier porosity was measured in accordance with Federal Test Method 5450 (Revised Mar. 18, 1992).

As can be see from Table II, the inner and outer wraps of the heavy grade sterilization system of the present invention provided an overall system with overall better grab tensile and peak energy values than the Baxter DualWrap® sterilization wrap. In addition, the heavy grade system of the present invention had a lower dry spore penetration rate and therefore a higher bacterial filtration efficiency than the Baxter material.

TABLE II

| Test Parameter | DualWrap® | | Kimguard One Step ™ HG[1] | |
|---|---|---|---|---|
| | Inner | Outer | Inner | Outer |
| Grab Tensile, lbs | | | | |
| MD | 14.4 | 27.5 | 37.1 | 45.4 |
| CD | 13.2 | 16.0 | 26.8 | 35.7 |
| Peak Energy, in-lbs | | | | |
| MD | 1.1 | 11.8 | 37.2 | 46.8 |
| CD | 1.6 | 18.4 | 32.4 | 46.1 |
| Dry Spore, ppt[2] | 10.6 | 18.4 | 2.6 | 1.4 |
| BFE[3], % | 73 | 56 | 78 | 73 |
| Frazier Porosity cu ft/sq ft/min. | 21.0 | 53.4 | 44.2 | 44.0 |
| Basis weight, osy | 1.55 | 2.02 | 1.89 | 2.49 |

[1]Heavy Grade - contains 0.5 osy of meltblown fiber, the remaining weight is spunbond fiber
[2]Particles per one-thousand
[3]Bacterial Filtration Efficiency Referring to Table III, the regular grade sterilization wrap system of the present invention when compared to the Baxter DualWrap® sterilization wrap provided comparable grab tensile values and better peak energy values. In addition, the regular grade sterilization wrap system had a lower dry spore penetration rate and thus a higher bacterial filtration efficiency due to the nature of the individual components than did the DualWrap® sterilization wrap.

TABLE III

| Test Parameter | DualWrap® | | Kimguard One Step ™ RG[1] | |
|---|---|---|---|---|
| | Inner | Outer | Inner | Outer |
| Grab Tensile, lbs | | | | |
| MD | 14.4 | 27.5 | 22.4 | 26.7 |
| CD | 13.2 | 16.0 | 14.2 | 20.2 |
| Peak Energy, in-lbs | | | | |
| MD | 1.1 | 11.8 | 17.3 | 24.4 |
| CD | 1.6 | 18.4 | 13.8 | 23.2 |

TABLE III-continued

| Test Parameter | DualWrap® | | Kimguard One Step ™ RG[1] | |
|---|---|---|---|---|
| | Inner | Outer | Inner | Outer |
| Dry Spore, ppt[2] | 10.6 | 18.4 | 0.8 | 1.2 |
| BFE[3], % | 73 | 56 | 72 | 75 |
| Frazier Porosity cu ft/sq ft/min. | 21.0 | 53.4 | 47.8 | 73.0 |
| Basis weight, osy | 1.55 | 2.02 | 1.44 | 1.43 |

[1]Regular Grade - the inner wrap contains 0.5 osy of meltblown fibers and the outer wrap contains 0.3 osy of meltblown fibers with the spunbond fiber weight making up the difference in total weight.
[2]Particles per one-thousand
[3]Bacterial Filtration Efficiency Actual in use product efficacy is the ultimate test of whether a product works. To determine the functionality of the sterilization wrap system of the present invention in protecting package contents from contamination, a study was performed on three sterilization wrap systems all of which were used to wrap packages which were subsequently sterilized using steam. For each of the three systems, 120 samples were prepared and tested in an effort to determine the overall efficacy of the present invention relative to each of the controls. As can be seen from Table IV, the first set of samples utilized the system of the present invention. The outer wrap 12 was a 1.4 ounces per square yard spunbond/meltblown/spunbond laminate including an inner meltblown layer with a basis weight of 0.3 ounces per square yard and two outer spunbond layers, each having a basis weight of 0.55 ounces per square yard. The 1.4 ounce per square yard inner wrap 14 was also a spunbond/meltblown/spunbond laminate including a meltblown layer having a basis weight of 0.5 ounces per square yard and two outer spunbond layers, each having a basis weight of 0.45 ounces per square yard. The outer wrap 12 was ultrasonically bonded to the inner wrap 14 in a manner similar to that shown in FIG. 1. Ultrasonic bonding techniques and equipment are well known.

Control I was two unattached sheets of a current Kimberly-Clark Corporation polypropylene sterilization wrap which historically has shown less than 3% contamination when using sequential wrapping techniques. Each of the unattached sterilization wrap sheets was made from a spunbond/meltblown/spunbond laminate having an approximate overall basis weight of 1.4 ounces per square yard including a 0.4–0.5 ounce per square yard meltblown layer and two approximately 0.45 ounce per square yard spunbond layers.

Control II was two unattached sheets of muslin cloth with each sheet being made from two layers of 140 thread count muslin cloth sewn together. Sterilized packages wrapped with two sheets of unattached muslin cloth have historically shown about 10%–26% contamination.

All 120 packages for each of the sample controls were prepared using a double sequential wrapping method, that is, folding one sheet around the package followed by repeating the process by folding a second sheet of wrap around the package. These packages were wrapped in this manner to represent the most commonly used method of wrapping (double, sequential wrapping). The 120 samples of the present invention was simultaneously wrapped with two sheets of wrap which were ultrasonically bonded together. All the packages, including the controls, were sterilized using steam. Once sterilized, the packages were sent from the Sterile-Processing Department of a hospital to the operating room and from the operating room back to storage to simulate a cancelled procedure and then back to the operating room within a time period of two days. Package contents were then microbiologically cultured to determine the percentage of contaminated packages. The results of this study are given in Table IV.

TABLE IV

EVENTS RELATED STERILITY EFFICACY STUDY RESULTS

|  | No. Packages Contaminated | % Packages Contaminated |
|---|---|---|
| Single Step Sterilization Wrap System (Ultrasonically fused polypropylene sterilization wrap) | 1/120 | 0.83 |
| Control I - Kimberly-Clark polypropylene sterilization wrap | 0/120 | 0 |
| Control II - 140 Thread Count Cloth | 12/120 | 10.0 |

As can be seen, the sterilization wrap system of the present invention only had one contaminated package out of 120 total packages, for a package contamination percentage of 0.83%. Control I had no contaminations and the Control II (cloth) system had 12 contaminations per 120 packages for a package contamination percentage of 10%. At a 95% confidence level, the contamination level of the sterilization wrap system of the present invention and Control 1 were not statistically different. At the same 95% confidence level, both the sterilization wrap system of the present invention and Control I had significantly lower contamination rates than Control II. As a result, it can be seen that using two attached sheets of sterile wrap in a simultaneous wrapping function protects packaged contents as well as double sequential wrapping with unattached sheets.

The amount of time necessary to wrap and open a package is another important feature of the present invention and is particularly important to hospitals in connection with the labor costs in preparing and opening hospital goods. To demonstrate packaging and opening time savings incurred when using the present invention, an in-hospital time study was conducted to compare the time it takes to wrap and open the system of the present invention discussed in Table IV and the control I system and the Control II system which were double sequentially wrapped and opened and also discussed in Table IV. As noted previously, the Control I and Control II systems were comprised of two sheets of sterilization wrap that were not attached to one another. The simultaneous wrapping method with the present invention and the double sequential method with the Control I and II wraps were performed on a variety of items including towel packs, basins and instrument trays. The results are shown in Table V below.

TABLE V

| SINGLE STEP STERILIZATION WRAP SYSTEM VS. | TIME SAVINGS | |
|---|---|---|
|  | WRAPPING | OPENING |
| Control I | 49% | 48% |
| Control II | 47% | 42% |

Based upon the time related study, the sterilization wrap system of the present invention provided a 49% savings of time in wrapping as compared to the Control I system and a 47% time savings as compared to the Control II system. With respect to the opening of the sterilized packages, the sterilization system of the present invention provided a 48% reduction in time for opening as compared to the Control I system and a 42% savings of time as compared to opening with respect to the Control II system. Consequently, the bonding together of the outer wrap 12 and inner wrap 14 of the sterilization wrap system of the present invention provides a real improvement in time savings with respect to the handling/wrapping and unwrapping of sterilized packages in the hospital. As a practical matter, an item can be wrapped and unwrapped in almost one half the time it takes with conventional double, sequential wrapping. Consequently, the present invention can and does provide a real time and cost savings to the end user.

Having thus described the invention in detail, it should be apparent that various modifications and changes can be made without departing from the spirit and scope of the present invention. For example, a wide variety of individual sterilization wraps have been described herein. Thus, a wide variety of combinations of inner and outer wraps are possible including combinations of both disposable and reusable sterile wrap sheets. The inner and outer wraps may be made from the same or different basis weight materials to engineer specific properties into each of the wraps. In addition, a wide variety of bonding techniques were also disclosed which may be used alone or in combination with each other to impart varying bond patterns to the sterilization wrap system of the present invention. Consequently, these and other modifications are contemplated to be within the spirit and scope of the following claims.

We claim:

1. A method of sterilizing an article comprising:
   providing an article;
   wrapping the article with a sterilization wrap which comprises
      an inner wrap sheet and an outer wrap sheet; and
         exposing the wrapped article to sterilizing conditions for a sufficient time such that the article is sterilized;
      wherein each sheet comprises a laminate which comprises a first spunbond layer, a meltblown layer and a second spunbond layer and
      the sheets are joined together at a plurality of bond sites which occupy no more than 50% of the surface area of either of the sheets such that said sheets are visually distinguishable as separate sheets; and
      wherein at least one pound tensile force is required to separate said joined sheets.

2. The method of claim 1 wherein said sterilizing conditions are steam sterilizing conditions.

3. The method of claim 1 wherein said sterilizing conditions are ethylene oxide sterilizing conditions.

4. The method of claim 1 wherein the inner wrap sheet and the outer wrap sheet each have a basis weight of between about 0.5 and about 3.5 ounces per square yard.

5. The method of claim 1 wherein each sheet has at least one edge and wherein at least one edge of each sheet is not joined to the other sheet.

6. The method of claim 5 wherein each sheet is similarly sized and wherein at least one edge of one of the sheets aligns with and is not joined to at least one edge of the other sheet.

7. The method of claim 1 wherein each sheet has at least one edge and wherein each sheet is similarly sized and wherein at least one edge of one of the sheets aligns with and is not joined to at least one edge of the other sheet.

8. The method of claim 7 wherein said edges which align and are not joined are further characterized as generally parallel edges.

9. A method of sterilizing an article comprising:

providing an article;

wrapping the article with a sterilization wrap which comprises an inner wrap sheet and an outer wrap sheet; and exposing the wrapped article to sterilizing conditions for a sufficient time such that the article is sterilized;

wherein each sheet comprises a laminate which is formed from a first spunbond layer, a meltblown layer and a second spunbond layer and the sheets are joined together at a plurality of bond sites which occupy no more than 50% of the surface area of either of the sheets such that said sheets are visually distinguishable as separate sheets;

wherein at least one pound tensile force is required to separate said joined sheets; and wherein each sheet has at least one edge, and wherein each sheet is similarly sized and wherein at least one edge of one of the sheets aligns with and is not joined to at least one edge of the other sheet and wherein said aligned and not joined edges are further characterized as generally parallel edges.

10. A method of sterilizing an article comprising:

providing an article;

wrapping the article with a sterilization wrap;

exposing the wrapped article to sterilizing conditions for a sufficient time such that the article is sterilized; and wherein the sterilization wrap comprises an inner wrap sheet and an outer wrap sheet;

wherein the sheets are joined together such that said sheets are visually distinguishable as separate sheets.

11. The method of claim 10 wherein the sheets are further joined together at a plurality of bond sites, said bond sites occupy no more than 50% of the surface area of either of the sheets.

12. The method of claim 10 wherein the grab tensile strength of one of the sheets is greater than the grab tensile strength of the other sheet.

13. The method of claim 10 wherein said sterilizing conditions are steam sterilizing conditions.

14. The method of claim 10 wherein said sterilizing conditions are ethylene oxide sterilizing conditions.

15. The method of claim 10 wherein the inner wrap sheet and the outer wrap sheet each have a basis weight of between about 0.5 and about 3.5 ounces per square yard.

16. The method of claim 10 wherein each sheet has at least one edge and wherein at least one edge of each sheet is not joined to the other sheet.

17. The method of claim 16 wherein each sheet is similarly sized and wherein at least one edge of one of the sheets aligns with and is not joined to at least one edge of the other sheet.

18. The method of claim 10 wherein each sheet has at least one edge and wherein each sheet is similarly sized and wherein at least one edge of one of the sheets aligns with and is not joined to at least one edge of the other sheet.

19. The method of claim 18 wherein said edges which align and are not joined are further characterized as generally parallel edges.

* * * * *